United States Patent [19]

Kumar

[11] Patent Number: 5,556,747
[45] Date of Patent: Sep. 17, 1996

[54] METHOD FOR SITE-DIRECTED MUTAGENESIS

[75] Inventor: Ramesh Kumar, Lawrenceville, N.J.

[73] Assignee: E. R. Squibb & Sons, Inc., Princeton, N.J.

[21] Appl. No.: 549,787

[22] Filed: Jul. 9, 1990

[51] Int. Cl.$^6$ .................. C12Q 1/68; C12P 19/34
[52] U.S. Cl. .................. 435/6; 435/91.1; 435/91.2; 435/172.1; 435/172.3
[58] Field of Search .................. 435/6, 27, 91.1, 435/91.2, 172.1, 172.3; 935/77, 78

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/91.2 |
| 4,683,202 | 7/1987 | Mullis | 435/91.2 |
| 4,800,159 | 1/1989 | Mullis et al. | 435/91.2 |

OTHER PUBLICATIONS

Mullis et al. Cold Spr Harbor. A4; 263–73 (1986).
Nelson et al. Anal. Biochem. 180: 147–51 (1989).
Hemsley et al. Nuc. Acid Res. 17(16):6545. (1989).
Kumar, R., Technique 1, 133–152 (1989) "The Technique of Polymerase Chain Reaction".
Sarkar, G. et al., BioTechniques 8, 404–407 (1990) "The Megaprimer Method of Site–Directed Mutagenesis".
Kunkel, T. A., Proc. Natl. Acad. Scit. USA 82, 488–492 (1985) "Rapid and Efficient Site–specific Mutagenesis without Phenotypic Selection".
Vallette, F., Nucl. Acids Res. 17, 723–733 (1989) "Construction of mutant and chimeric genes using the polymerase chain reception".
Higuchi, R. et al., Nucl. Acids Res. 16, 7351–7367 (1988) "A general method of in vitro preparation and specific mutagenesis of DNA fragments: study of protein and DNA interactions".
Kadowaki, H. et al., Gene 76, 161–166 (1989) "Use of polymerase chain reaction catalyzed by Taq DNA polymerase for site–specific mutagenesis".
Dulau, L. et al., Nucl. Acids Res. 17, 2873 (1989) "Directed mutagenesis using PCR".
Ho, S. N. et al., Gene 77, 51–59 (1989) "Site–directed mutagenesis by overlap extension using the polymerase chain reaction".
Yon, J. and Fried, M., Nucl. Acids Res. 17, 4895 (1989) "Precise gene fusion by PCR".
Mole, S. E. et al., Nucl. Acids Res. 17, 3319 (1989) "Using the polymerase chain reaction to modify expression plasmids for epitope mapping".
Kammann, M. et al., Nucl. Acids Res. 17, 5404 (1989) "Rapid insertional mutagenesis of DNA by polymerase chain reaction (PCR)".
Horton, R. M. et al., BioTechniques 8, 528–535 (1990) "Gene splicing by overlap extension: Tailor–made genes using the polymerase chain reaction".

*Primary Examiner*—Kenneth R. Horlick
*Attorney, Agent, or Firm*—Timothy J. Gaul; James M. Bogden

[57] ABSTRACT

A method for site-directed mutagenesis using a third mutagenic primer in a polymerase chain reaction (PCR) based methodology.

19 Claims, 8 Drawing Sheets

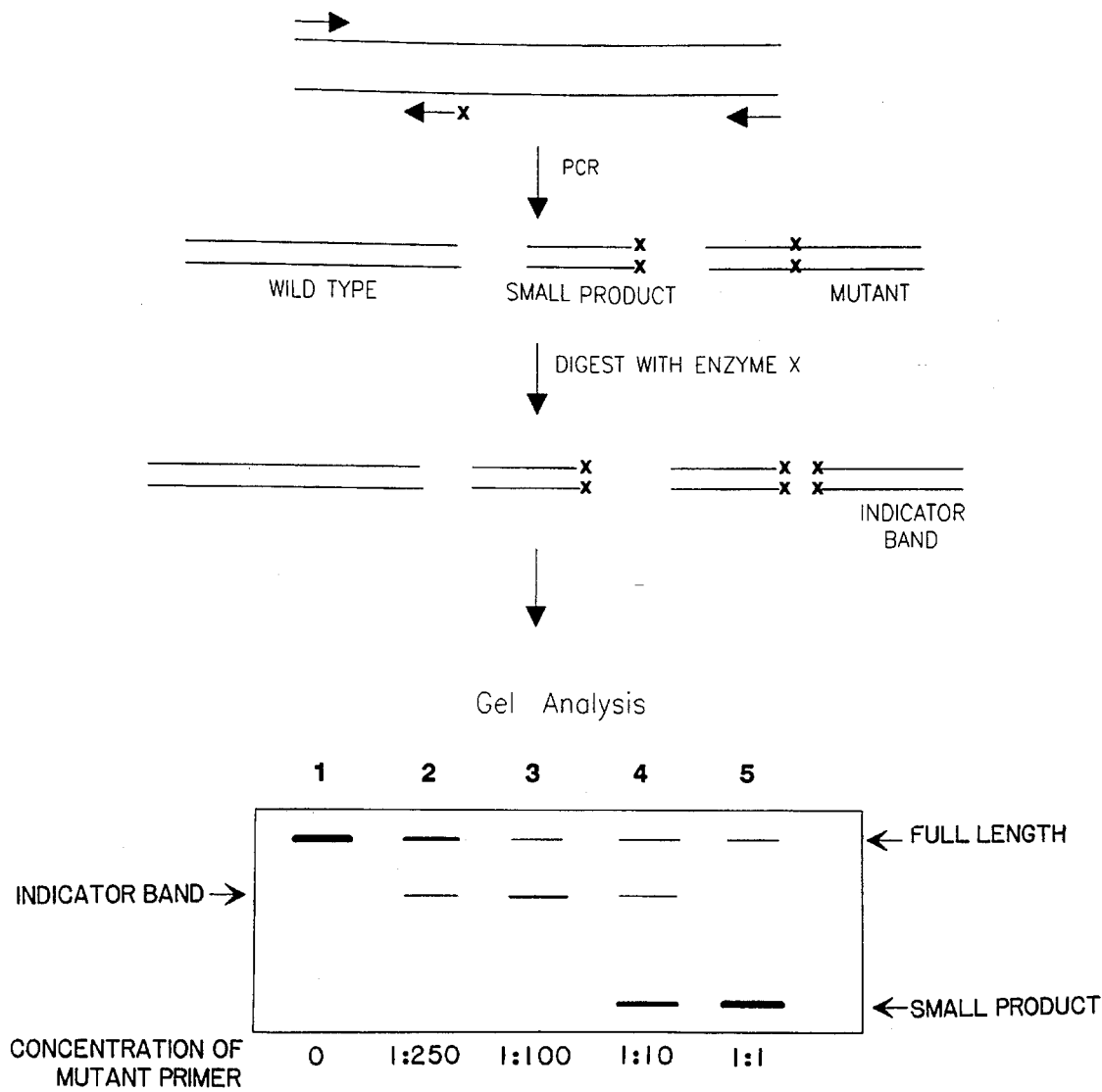

| CYSTEINE RESIDUE NO. | SEQUENCE | NUMBER OF MISMATCHES |
|---|---|---|
| 1. 36 | | 3 |
| 2. 40 | | 2 |
| 3. 41 | | 1 |
| 4. 50 | | 2 |
| 5. 152 | | 4 |
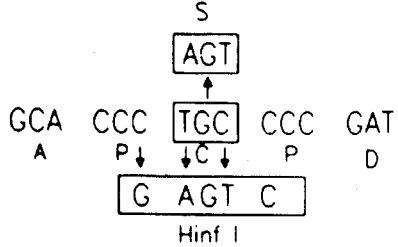
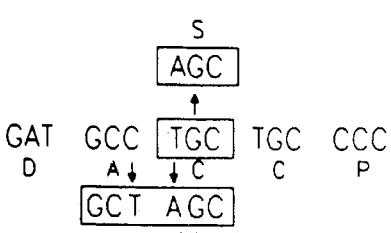
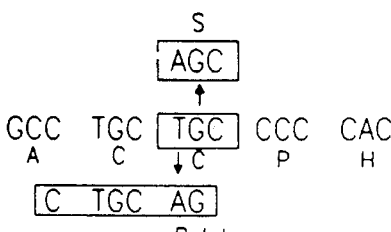
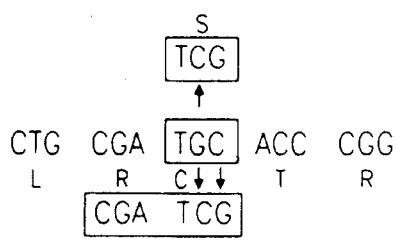
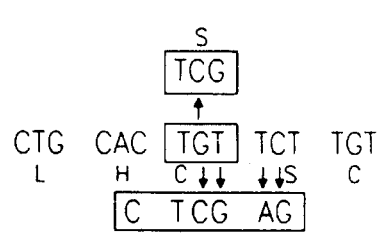
FIG. 7A

METHOD FOR SITE-DIRECTED MUTAGENESIS

BACKGROUND OF THE INVENTION

A popular approach in molecular biology involves the introduction of specific mutations in cloned genes for the analysis of phenotypes. Shortle, D., J. Biol. Chem. 264, 5315–5318 (1989). This reverse-genetic approach, employing site-directed mutagenesis, has facilitated the elucidation of structure-function relationships for a large number of genes. Such methods have also been successfully used for the design of desired characteristics into gene products for use in research and its applications. In some instances, such experiments have revealed intricacies of functional organization that were not apparent from the primary sequence or expression patterns. Matthews, B., Biochemistry 26, 6885–6887 (1987).

Methods of site-directed mutagenesis have evolved rapidly since the initial description of this concept. Smith, M., Annv. Rev. Genet. 19, 423–462 (1985). A common feature of the available methods is the use of synthetic oligonucleotides carrying the desired changes in the nucleotide sequence at the site of mutagenesis. This "mutant" oligonucleotide is incorporated into the sequence of interest by replacing the normal sequences with the designed oligonucleotide. This is accomplished by in vitro enzymatic DNA synthesis. A second step that requires the propagation and resolution of mutant and wild-type sequences in bacteria can greatly influence the rate of mutagenesis. Recently, the use of specially selected strains of *E. coli* that will allow enrichment of mutant molecules has improved the efficiency of mutagenesis. Kunkel, T. A., Proc. Natl. Acad. Sci. USA 82, 480–492 (1985).

Both the efficiency and the speed of mutagenesis have been improved by the introduction of methods based on the Polymerase Chain Reaction (PCR). Saiki, R. K. et al., Science 239, 487–491 (1986). Several methods based on PCR have been described that allow the introduction of mutations into one of the two primers used for the amplification of DNA. Higuchi, R. et al., Nucl. Acids Res. 16, 7351–7367 (1988); Valette, F. et al., Nucl. Acid Res. 17, 723–733 (1989); Kadowaki, H. et al., Gene 76, 161–166 (1989); Dubau, L. et al., Nucl. Acids Res. 17, 2873 (1989). However, these methods are limited to the mutagenesis of the sequences located at the termini of the amplified sequences. Other methods that permit the modification of amplified sequences via the use of primers that overlap two non-contiguous sequences during amplification, have been described. However, such methods are limited by the nature of the sequence overlaps and require multiple steps. Ho, S. N. et al., Gene 77, 51–59 (1989); Yon, J. et al., Nucl. Acids Res. 1–7, 4895 (1989); Mole, S. E. et al., Nucl. Acids Res. 17, 3319 (1989); Kammann, M. et al., Nucl. Acids Res. 17, 5404 (1989).

A method that would permit the incorporation of desired mutations at any site in the target of PCR amplification would greatly expand the utility of PCR mutagenesis.

SUMMARY OF THE INVENTION

The present invention concerns a method for the incorporation of mutations into one or both strands of a target double stranded DNA molecule derived from a starting nucleic acid molecule comprising:

(a) contacting the target double stranded DNA molecule derived from a starting DNA molecule with two primers flanking the nucleotides to be mutated and a mutagenic third primer; and (b) subjecting the resulting reaction mixture to a sufficient number of rounds of PCR to generate the mutations in one or both strands of the target double stranded DNA molecule and amplify the mutated DNA sequences.

The present invention further concerns a method for the incorporation of mutations into one or both strands of a target double stranded DNA molecule derived from a starting nucleic acid molecule comprising:

(a) separating the strands of the target double stranded DNA molecule by physical, chemical or enzymatic means;

(b) contacting the resulting single stranded DNA molecules with two oligodeoxyribonucleotide primers flanking the nucleotides to be mutated and a mutagenic third oligodeoxyribonucleotide primer under conditions such that an extension product of each primer is synthesized using an inducing agent;

(c) separating the primer extension products by physical, chemical or enzymatic means from the templates on which they are synthesized; and (d) treating the single stranded molecules generated from step (c) with the three primers of step (b) under conditions such that a primer extension product is synthesized using an inducing agent.

DESCRIPTION OF THE DRAWINGS

FIG. 2: RFLP analysis of site-directed mutations generated by PCR. PCR amplification coupled with mutagenesis results in the generation of full-length wild-type and mutant, and small products. The mutagenic primer is designed to generate diagnostic RFLPs associated with the created mutation. Digestion with a specific restriction enzyme (designated X) followed by electrophoretic analysis is used to distinguish mutant and wild-type products. In the schematic depiction the mutant, but not the wild-type PCR products, upon digestion, yield a novel (indicator) band diagnostic of the mutation. The relative intensity of this indicator band is a measure of the efficiency of mutagenesis and is related to the concentration of the third (mutagenic) primer in PCR.

DETAILED DESCRIPTION OF THE INVENTION

The present invention concerns a method for the incorporation of mutations into one or both strands of a target double stranded DNA molecule derived from a starting nucleic acid molecule comprising:

(a) contacting the target double stranded DNA molecule derived from a starting nucleic acid molecule with two primers flanking the nucleotides to be mutated and a mutagenic third primer; and (b) subjecting the resulting reaction mixture to a sufficient number of rounds of PCR to generate the mutations in one or both strands of the target double stranded DNA molecule and amplify the mutated DNA sequences.

The present invention further concerns a method for the incorporation of mutations into one or both strands of a target double stranded DNA molecule derived from a starting nucleic acid molecule comprising:

(a) separating the strands of the target double stranded DNA molecule by physical, chemical or enzymatic means;

(b) contacting the resulting single stranded DNA molecules with two oligodeoxyribonucleotide primers flanking the nucleotides to be mutated and a mutagenic third oligodeoxyribonucleotide primer under conditions such that an extension product of each primer is synthesized using an inducing agent;

(c) separating the primer extension products by physical, chemical or enzymatic means from the templates on which they are synthesized; and (d) treating the single stranded molecules generated from step (c) with the three primers of step (b) under conditions such that a primer extension product is synthesized using an inducing agent.

The method of the present invention incorporates an important modification in a conventional PCR protocol to allow PCR linked site-directed mutagenesis. This modification involves the use of three primers simultaneously in the PCR. One of the three primers is located between the other two amplification primers and carries the desired mutations. During DNA amplification, under appropriate conditions, this mutagenic primer is incorporated into a subset of amplification products. This method allows incorporation of desired mutations at any site in the target of PCR amplification.

A second, optional embellishment, based on the design of diagnostic restriction sites at the site of mutation, permits easy identification of mutants and the evaluation of the efficiency of mutagenesis. This method is widely applicable to the modification of coding sequences, or the creation or extinction of restriction sites, and can be used for direct mutagenesis of genomic DNA or mRNA sequences without prior cloning.

Figure 1:
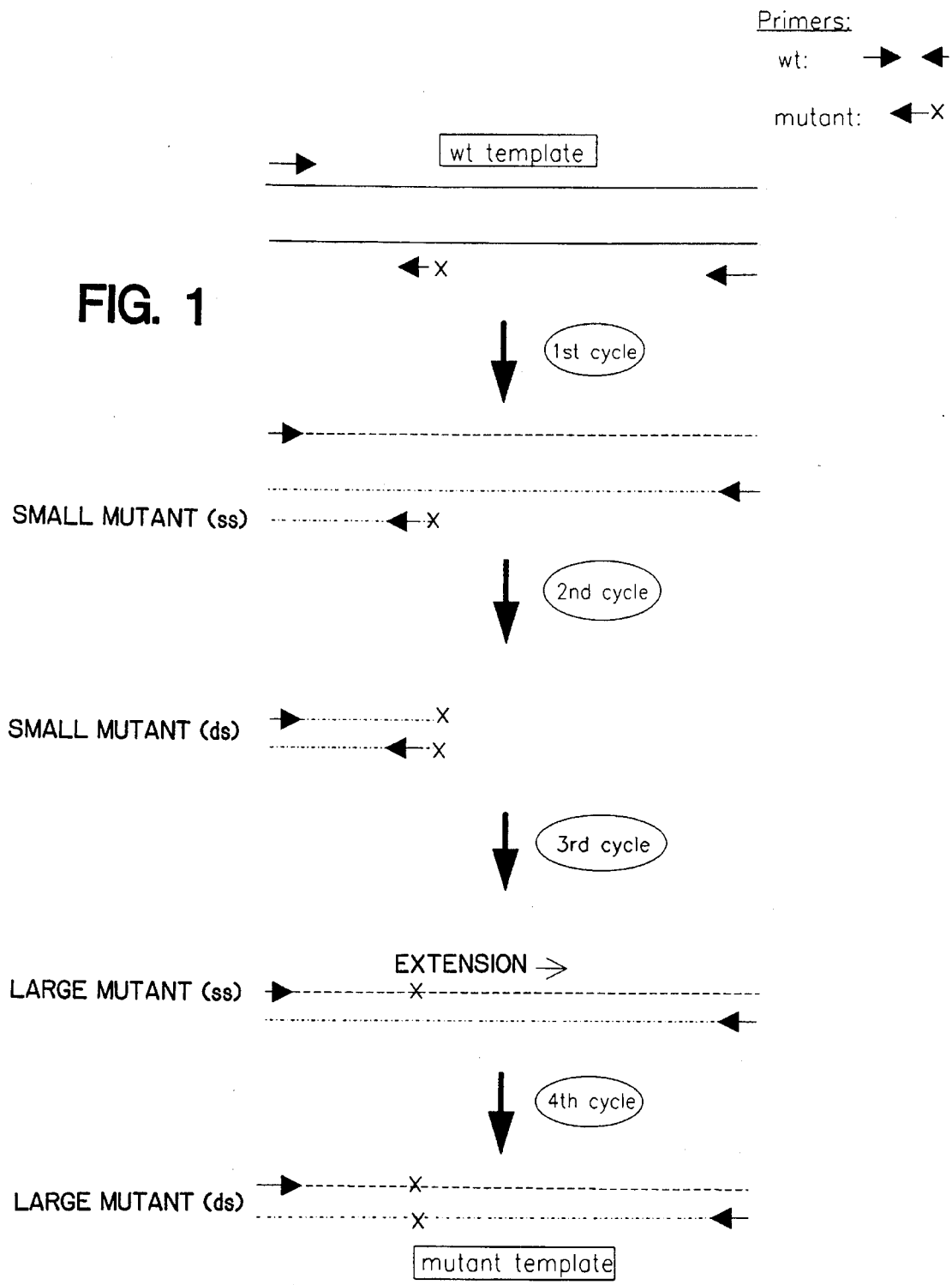
FIG. 1: Schematic representation of the protocol for mutagenesis. Two conventional PCR primers (Wt) and an internal primer carrying the desired mutation (marked with an X) are used to amplify a single double-stranded hypothetical target. The extension products of these three primers after the first cycle are shown. Only the fate of the mutant primer extension product is depicted over 3 additional cycles of PCR. In the second cycle, the extension product of the mutant primer leads to the synthesis of a double stranded (ds) molecule carrying mutations on both strands (small mutant, ds). One of the two strands of this product is used in the third cycle in a primer extension reaction using wild-type DNA template, resulting in the generation of a single-stranded full length mutant template (large mutant). This is then copied to generate a ds mutant template that can be amplified by PCR.

The method of site-directed mutagenesis of the present invention utilizes three primers in a polymerase chain reaction in order to introduce site-directed mutations contained in one primer into specific targets. A schematic diagram depicting the principle of the described method is shown in FIG. 1. Two primers flanking the sequences that include the target of mutagenesis are used in PCR. The third PCR primer is the mutagenic primer that contains the desired nucleotide changes. This primer can be designed to be complementary to either strand of DNA.

The mechanism by which the mutant third primer is incorporated into the PCR product is shown in FIG. 1. The initial round of PCR results in the generation of a small DNA (single stranded) containing the mutant primer at its 5' end. This strand can be used as a template by one of the PCR primers to generate small double stranded molecules that carry the mutation on both strands of the DNA (at the 5' and 3' ends of the two strands). The new DNA strand carrying the mutation near its 3' end can prime a longer DNA strand synthesized by conventional PCR in a previous cycle or present in the original DNA template. Primer extension generates target length single stranded products that carry the mutation. These products (full length) can then be used as templates by the two PCR primers to generate full length molecules that carry site-directed mutations.

In practicing the process of the present invention, it is desirable that a double stranded DNA molecule be employed as the template for mutagenesis. However, in general, any nucleic acid molecule in purified or non-purified form, can be utilized as the starting nucleic acid, provided that it is suspected of containing the specific nucleic acid sequence which is desired to be mutated, and can be converted into a double stranded DNA molecule. Thus, the starting nucleic acid may be, for example, DNA or RNA, including messenger RNA (mRNA), which DNA or RNA may be single stranded or double stranded. In addition, the starting nucleic acid may be a DNA-RNA hybrid. In the case when the starting nucleic acid is not a double stranded DNA molecule, it must first be converted to a double stranded DNA molecule. For example, if the starting nucleic acid is a single stranded mRNA, it must first be converted to a single stranded DNA molecule (e.g., by using reverse transcriptase), which must then be converted to a double stranded DNA molecule (e.g., by using Taq DNA polymerase). The nucleic acid sequence to be mutated may be only a portion of the starting nucleic acid molecule, or may constitute the entire starting nucleic acid molecule. It is not necessary that the starting nucleic acid molecule be present initially in pure form; for example, it may be a minor fraction of a complex mixture, such as a portion of a β-adrenergic receptor gene contained in human genomic DNA, or can be mRNA contained in a crude cellular extract. The starting nucleic acid molecule may be obtained from a variety of sources, including, for example, plasmid DNA, cloned DNA, complementary DNA (cDNA), genomic DNA, and natural DNA from virtually any source, including bacteria, yeast, viruses and higher organisms such as plants and animals.

The primers of the present invention (both flanking and mutagenic) must be capable of acting as points of initiation of DNA synthesis when placed under conditions in which synthesis of a primer extension product which is complementary to a DNA strand is induced, i.e., in the presence of nucleotides and an inducing agent such as DNA polymerase and at a suitable temperature and pH. The primers are preferably single stranded for maximum efficiency in mutagenesis and amplification, but may alternatively be double stranded. If double stranded, the primer is first treated to separate its strands before being used to prepare extension products. Preferably, the primers are oligodeoxyribonucleotides. The primers must be sufficiently long to prime the synthesis of extension products in the presence of the inducing agent. The exact lengths of the primers will depend on many factors, including the reaction temperature and the source of the primer.

Typically, the primers may range in length from about 15 to about 70 nucleotides, and preferably range from about 20 to about 30 nucleotides.

The number of mismatches (i.e., mutations) in the third mutagenic primer is not critical. It is only necessary that the mutagenic primer be sufficiently complementary to its respective DNA strand so that it is able to hybridize thereto. In general, up to about 20% mismatches may occur in the third mutagenic primer without affecting its ability to hybridize with its respective DNA strand.

It is generally preferred that the flanking primers contain no mismatches (i.e., be exactly complementary to their respective DNA strands) so that all mutations arise from the mutagenic third primer. However, as with the mutagenic primer, it is only necessary that the flanking primers be sufficiently complementary to their respective DNA strands so that they are able to hybridize thereto. In this instance, the flanking primers may also be used to introduce mutations along with the mutagenic third primer.

The oligonucleotide primers may be prepared using any suitable method, for example, by chemical synthesis using the phosphotriester and phosphodiester methods, or automated embodiments thereof. It is also possible to use a primer which has been isolated from a biological source (such as a restriction endonuclease fragment).

Any specific DNA sequence derived from a starting nucleic acid molecule can be mutated by the process of the present invention. It is only necessary that a sufficient number of bases of the sequence be known in sufficient detail so that two flanking primers and a mutagenic primer can be prepared which will hybridize to the desired portions of the specific sequence. The greater the knowledge about the bases of the DNA sequence, the greater can be the specificity of the primers for the target DNA sequence, and thus the greater the efficiency of the process.

The PCR methodology used to perform the mutagenesis process of the present invention will now be described. The target double stranded DNA molecule must first be separated before it can be used as the template, either as a separate step or simultaneously with the synthesis of the primer extension products. This strand separation can be accomplished by any suitable denaturing method, including physical, chemical or enzymatic means. For example, the strands of the DNA may be separated by heating the DNA until it is completely (>99%) denatured. Typical heat denaturation may involve temperatures ranging from about 80° to 105° C. for times ranging from about 1 to 10 minutes.

When the complementary strands of the target double stranded DNA are separated, whether the starting nucleic acid was originally double or single stranded, the strands are ready to be used as a template for mutagenesis of the double stranded DNA. This mutagenesis process can be performed as follows. Generally it occurs in a buffered aqueous solution, preferably at a pH of 7–9, most preferably about 8. Preferably, molar excesses (for cloned DNA, usually 1000:1 primer: template, and for genomic DNA, usually about $10^6$:1 primer:template) of the three oligonucleotide primers are added to the buffer containing the separated template strands. As a practical matter, the amount of primer added will generally be in molar excess over the amount of complementary strand (template) when the sequence to be amplified is contained in a mixture of complicated long-chain DNA strands. A large molar excess is preferred to improve the efficiency of the process.

The deoxyribonucleoside triphosphates dATP, dCTP, dGTP and dTTP are also added to the mutagenesis reaction mixture in adequate amounts and the resulting solution is heated to about 90° C. –100° C. for about 1 to 10 minutes, preferably for about 1 to 4 minutes. After this heating period, the solution is allowed to cool to room temperature, which is preferable for the primer hybridization. To the cooled mixture is added an appropriate agent for inducing or catalyzing the primer extension reaction, and the reaction is allowed to occur under conditions known in the art. This synthesis reaction may occur at from room temperature up to a temperature above which the inducing agent no longer functions efficiently.

The inducing agent may be any compound or system which will function to accomplish the synthesis of primer extension products, although enzymes are generally employed. Suitable enzymes for this purpose include, for example, *E. coli* DNA polymerase I, the Klenow fragment of *E. coli* DNA polymerase I, T4 DNA polymerase, other available DNA polymerases, reverse transcriptase, and other enzymes, including heat-stable enzymes such as Taq DNA polymerase, which will facilitate combination of the nucleotides in the proper manner to form the primer extension products which are complementary to each DNA strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the other direction, using the same process as described above.

The newly synthesized DNA strand and its complementary strand form a double stranded molecule which is used in the succeeding steps of the process. Thus, the above steps of strand separation and extension product synthesis can be repeated as often as needed to produce the desired quantity of the specific mutant DNA sequence. The amount of the specific mutant DNA sequence produced will accumulate in an exponential fashion. As noted above, at least three rounds of PCR are necessary to incorporate the desired mutations into one strand of the double stranded DNA template, while four rounds of PCR are necessary to incorporate the desired mutations into both strands.

The present invention can be performed in a step-wise fashion where after each step new reagents are added, or simultaneously, where all reagents are added at the initial step, or partially step-wise and partially simultaneous, where fresh reagent is added after a given number of steps. It is preferred that the method of the present invention be performed simultaneously. If a method of strand separation, such as heat, is employed which will inactivate the inducing agent, as in the case of a heat-labile enzyme, then it is necessary to replenish the inducing agent after every strand separation step. If heat is used for denaturation in a simultaneous process, a heat-stable inducing agent such as a thermostable polymerase (e.g., Taq DNA polymerase) may be employed which will operate at an elevated temperature, preferably 65°–90° C. depending on the inducing agent, at which temperature the DNA will consist of single and double strands in equilibrium. For smaller lengths of DNA, lower temperatures of about 50° C. may be employed. The upper temperature will depend on the temperature at which the enzyme will degrade or the temperature above which an insufficient level of primer hybridization will occur. Each step of the process will occur sequentially notwithstanding the initial presence of all the reagents. Additional materials may be added as necessary. After the appropriate length of time has passed to produce the desired amount of the specific mutant DNA sequence, the reaction may be halted by inactivating the enzymes in any known manner or separating the components of the reaction mixture.

Previously described methods for the introduction of mutations using PCR art are limited to modification of the terminal regions of the amplified DNA target, or require multiple steps of amplification. In contrast, the method of the present invention may be performed as a simultaneous, single step method, although it may be performed in a step-wise fashion as well, and is not limited to the mutagenesis of the terminal regions of the amplified DNA; the mutation can be located anywhere inside the PCR target.

It should be evident from the above that the above process results in a mixture of reaction products. Thus, once the desired mutant DNA molecules have been created, various methods must be used for distinguishing mutant DNA molecules from wild-type DNA molecules. At least two principal methods may be employed.

First, the oligonucleotide employed for the creation of the mutant can also be used for screening by hybridization under stringent conditions. Such methods use radioactively labeled oligonucleotides, and by nature are technically demanding, especially when the method involves only a single base change.

It is preferred that mismatches resulting in the desired mutations be designed to create a diagnostic restriction enzyme site at the site of mutation. In this case, the third mutagenic primer in the PCR reaction is designed to generate not only the specific mutation of interest but also the diagnostic restriction enzyme site. Alternatively, an existing restriction enzyme site may be eliminated through mutation. The created or eliminated diagnostic restriction fragment length polymorphism (RFLP) can then be used to monitor the occurrence and the efficiency of mutagenesis in PCR, and can be used to facilitate the screening of recombinant clones. FIG. 2 depicts a procedure for the evaluation of the efficiency of mutagenesis using a designed RFLP created by the incorporation of the mutant primer in the PCR product.

The amplified DNA is first digested with the restriction enzyme. The undigested and digested PCR products are compared after electrophoresis. The created RFLP permits the identification of a new DNA digestion product that is an indicator of mutagenesis. Comparison of the ratio of this indicator band and the full-length PCR product can permit quantification of the efficiency of mutagenesis.

This approach is most suitable for the screening of protein coding sequences where the degeneracy of the genetic code allows flexibility in the design of mismatches required for generating RFLP's.

The method of the present invention has a wide variety of potential applications. For example, the ability to use sequencing primers in amplification can make it cost-effective to design and test multiple primers for mutagenesis. The capability of directly mutating genomic DNA and cDNA should expedite a variety of experiments, including the tailoring of uncloned sequences from crude templates, easy analysis of related genes and the engineering of genes at the single-cell level. It will also facilitate the rapid elimination of undesirable restriction sites, introduction of appropriate signals and the precise segmentation of cloned sequences that lack convenient restriction enzyme sites. The method of the present invention can also be used to generate heteroduplex DNA molecules containing a mutated DNA strand hybridized to a non-mutated (wild type) DNA strand.

The only limits of the method of the present invention are the constraints of PCR amplification. It has been suggested that the size of the amplified target should be limited to 1–2 Kb because of concern over errors in misincorporation, even though the error rate has been estimated to be less than 1 in 10,000. However, future improvements in the enzymology of PCR should permit access to larger targets such as complete cDNAs or genomic clones.

The following examples are further illustrative of the present invention. These examples are not intended to limit the scope of the present invention, and provide further understanding of the invention.

EXAMPLE 1

Polymerase Chain Reaction

PCR was performed as described recently [Kumar, R., Technique 1, 133–152 (1989)]. The sequences of the various primers used are shown in Table 1. Most reactions included three primers (see FIG. 1), including two primers that are located at either end of the target of amplification. The third primer carrying the desired nucleotide mismatches was at the site of mutagenesis and was located between the flanking amplification primers. In general, primers were 20–30 nucleotides in length and were synthesized on an Applied Biosystems Model 280 B DNA synthesizer (Applied Biosystems, Inc., Foster City, Calif.). Primers were purified by standard denaturing polyacrylamide gel electrophoresis. [See, Maniatis et al., *Molecular Cloning: A Laboratory Manual*, Cold Spring Harbor Laboratory, Cold Spring Harbor, N.Y. (1982); Auschel, F. M. et al., eds., Current Protocols in Molecular Biology, John Wiley & Sons, NY (1987)]. Primers were dissolved in distilled water to a final concentration of 200–400 ng/ml.

In all cases, PCR was carried out essentially as suggested by the GENE-AMP kit's manufacturer (Perkin-Elmer/Cetus, Norwalk, Conn.). Amplification consisted of 30 cycles unless otherwise indicated. Each cycle consisted of melting at 94° C. for 1 minute, annealing at 50° C. for 2 minutes and polymerizing at 72° C. for 3 minutes. The polymerization time at 72° C. was extended by 5 seconds after each cycle. In each PCR reaction mixture, 0.5 μg of template DNA, approximately 1 μg of the two flanking primers and 4 to 1000 ng of the mutagenic third primer were used. All reactions were in a volume of 100 μl, and included 5 units of Taq polymerase (Perkin-Elmer/Cetus) and 0.25 mM each dATP, dGTP, dCTP and dTTP in 50 mM KCl, 10 mM Tris (pH 8.4), 2.5 mM $MgCl_2$, 0.1 mg/ml gelatin, 0.01% Tween-20 and 0.01% NP40. Amplified products were stored at −20° C.

TABLE 1

| Sequences of primers used in this study |
|---|
| A. trk protooncogene |
| i) PCR (Flanking) |
| #1709 5'-GGCTGGATCCTCACAGAGCTGGA-3' |
| #1712 5'-TCGGGTCCATGGGATCGGAGG-3' |
| ii) Mutagenic |
| #2039 5'-GAGGCGCAGACTCCCGTGCCGCAC-3' |
| #2040 5'-GTGCGGCACGGGAGTCTGCGCCTC-3' |
| B. $\beta_2$-adrenergic receptor |
| i) PCR (Flanking) |
| #257 5'-CCGCGCCATGGGACAACCCGGGAACG-3' |
| #221 5'-AAACTTACGAATTCCATGCAAAGAGG-3' |
| ii) Mutagenic |
| #433 5'-CCGCAGGTCTTCCAAGTTCTGCTTGAAGGAG-3' |
| C. Universal (M13) |
| Forward: 5'-CGCCAGGGTTTTCCCAGTCACGAC-3' |
| Reverse: 5'-AGCGGATAACAATTTCACACAGGA-3' |

EXAMPLE 2

Restriction Digestion

An aliquot (generally 10 μl of the 100 μl reaction mixture) was subjected to digestion with the appropriate restriction enzyme, following the restriction enzyme manufacturer's (New England Biolabs, Beverly, Mass.; Stratagene, La Jolla, Calif.) directions in a 25 μl reaction volume. In parallel, another aliquot was incubated in the restriction enzyme buffer. Incubations were for 2–16 hours at 37° C. Samples were resolved by electrophoresis in horizontal 1.0% agarose gels and DNA was visualized by ethidium bromide or methylene blue staining [Young-Sharp, D. and Kumar, R., Technique 1, 183–187 (1989)].

EXAMPLE 3

Cloning and Analysis

Amplified DNA was deproteinized and digested with the appropriate restriction enzymes as described in Protocol 1 in Kumar, R., Technique 1, 133–152 (1989). The pUC12N cloning vector was prepared after restriction digestion and gel purification. DNA ligations were performed using T4 DNA ligase and buffer (Bethesda Research Labs, Gaithersburg, Md.) as described in Protocol 1 in Kumar, R., Technique 1, 133–152 (1989). Competent *E. coli*, strain DH5a (Bethesda Research Labs) was transformed with DNA as suggested by the manufacturer, and the recombinant clones were identified by a blue-white selection using isopropyl thio galactoside (IPTG) and X-gal (Bethesda Research Labs). Plasmid DNA was prepared by the boiling method as described in Ausubel, F. M. et al., Current Protocols in Molecular Biology, Green Publishing Associates, New York, N.Y. (1988). DNA sequence analysis was performed by the dideoxy chain termination procedure using a reagent kit (Sequenase kit, U.S. Biochemicals, OH). Primers utilized in sequencing included the M13 forward and reverse primers (New England Biolabs) and 4 primers located 250 bp apart in the trk gene coding sequences used in this study. A portion of the sequencing was performed using the Dupont Genesis 2000 automated sequencing system (Dupont, Wilmington, Del.).

EXAMPLE 4

Production of Mutations

Figure 3A:
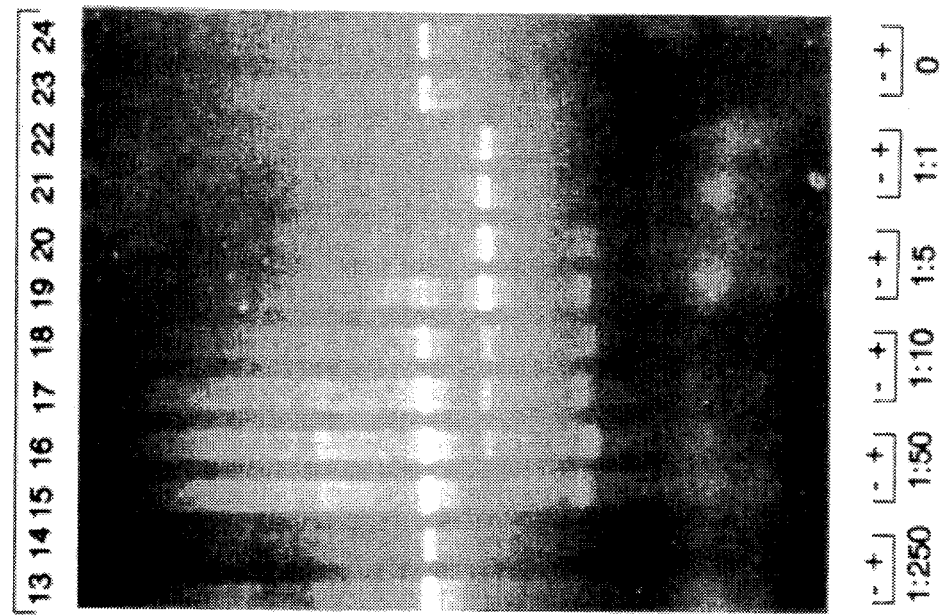
FIGS. 3A and 3B: Rate of mutagenesis is influenced by the concentration of the third primer. PCR amplification of a 1.1 kb segment of the human trk protooncogene was carried out with primers 1709 and 1712 at a 1:1 ratio and either mutagenic primer 2039 (Panel A) or 2040 (Panel B) at various concentrations. These concentrations are indicated at the bottom of the pictures. 0=no third primer used. The mutagenic primers were designed to create a novel HinF I site diagnostic of a T→A mutation resulting in the substitution of a Cys encoding triplet TGC with a serine encoding triplet (AGC). Amplified DNA was either digested with HinF I (+) or incubated in restriction-enzyme buffer (−) followed by electrophoresis in a 1.2% agarose gel. The migration of the (~750 bp) band is shown with an arrow. The mobility of θX Hae III DNA size markers are shown on the right.
Figure 3B:
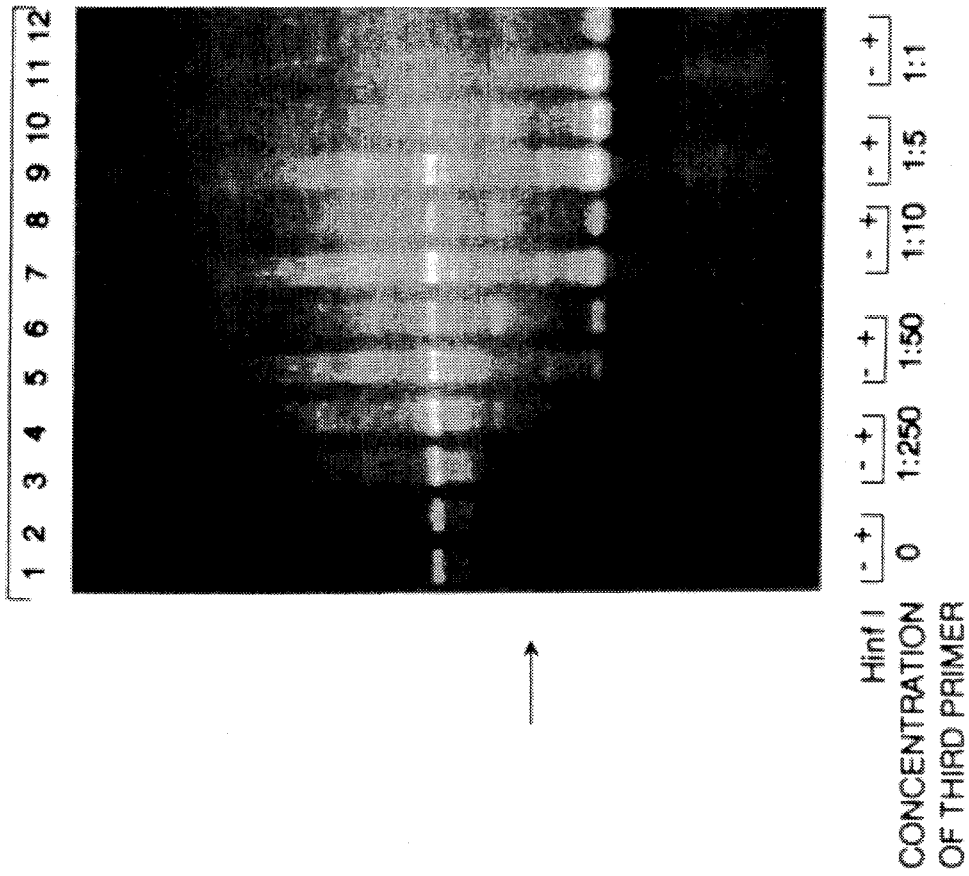

To demonstrate the method, the human trk protooncogene was used as a model system. The sequences of primers used for amplification and mutagenesis are shown in Table 1. FIGS. 3A and 3B depict the results of an experiment where a 1.1 Kb DNA fragment of the human trk protooncogene (nucleotides 771–1881) [See, Martin-Zanca, D. et al., Molecular and Celluar Biology 9, 24–33 (1989)] was amplified in order to mutate a TGC triplet encoding a Cys residue located between nucleotides 1035–1037. Two 24 mer oligonucleotides were designed that are complementary to the sequences surrounding the TGC triplet encoding the Cys residue. Primer 2039, complementary to the antisense strand, contains a T→A mismatch and primer 2040, complementary to the sense strand, contains A→T mismatch in the first nucleotide of the TGC triplet. Both mismatches were designed to mutate the TGC triplet to AGC, resulting in a Cys→Ser change in the encoded protein product. The mismatch was also designed to create a unique HinF I site in the amplified 1.1 Kb DNA segment.

The procedure was tested using a cDNA clone of the human trk gene as a template in a 40 cycle PCR amplification. In two separate sets of reactions (FIGS. 3A and 3B), two flanking primers (1709 and 1712, Table 1) and either of the two mutant primers 2039 and 2040 were used. Four different concentrations of the mutant primer were tested. The third mutant primer was used at 1:250, 1:50, 1:10, 1:5 or 1:1 ratio with respect to the two PCR primers. The efficiency of mutagenesis was monitored by HinF I digestion of the amplified DNA. The concentration of the mutant primer in the three primer PCR is a key determinant of the efficiency of mutagenesis.

As shown in FIGS. 3A and 3B, mutant products are generated when the mutagenic primer is used at 1:250, 1:50, 1:10, ratios. In this range, the fraction of mutant molecules in the population correlates with the amount of mutant primer used. The maximum amounts of mutant molecules were observed at the 1:50 and the 1:10 ratios when primer 2039 was used for mutagenesis (FIG. 3A). For primer 2040, the optimal ratio for mutagenesis was 1:50 (FIG. 3B). The production of full-length molecules was reduced when the mutant primer was used at higher concentrations (1:5 or 1:1). Although both mutagenic primers could be incorporated in the PCR product, some reactions containing primer 2040 also generated a smaller aberrant product (see FIG. 3B). This is a primer-related artefact and is observed with some but not all primers in PCR. Careful choice of the primers, coupled with comparison of undigested and digested amplification products, can circumvent such artefacts.

EXAMPLE 5

Cloning and Analysis of Mutants

To test the frequency of mutagenesis, the PCR products were cloned into pUC12N vectors digested with Nco I and Bam HI. One μg of pUC12N was digested for 1 hour at 37° C. with 10 units each of Nco I and Bam HI. The digested DNA (2.5 kb) was purified by electrophoresis in a 1.0% agarose gel and electroelution (See, Maniatis et al., supra).

50 ng of this vector and 100–200 ng of the PCR products (digested with Nco I and Bam HI) were ligated at 16° C. for 16 hours using T4 DNA ligase (Bethesda Research Labs) in a 20 μl reaction using buffer supplied by Bethesda Research Labs. Colonies were plated on plates containing ampicilin, X-gal and IPTG for blue/white selection of recombinants. The white colonies were picked and plasmid preparations were analyzed by restriction enzyme digestion and electrophoresis.

Figure 4B:
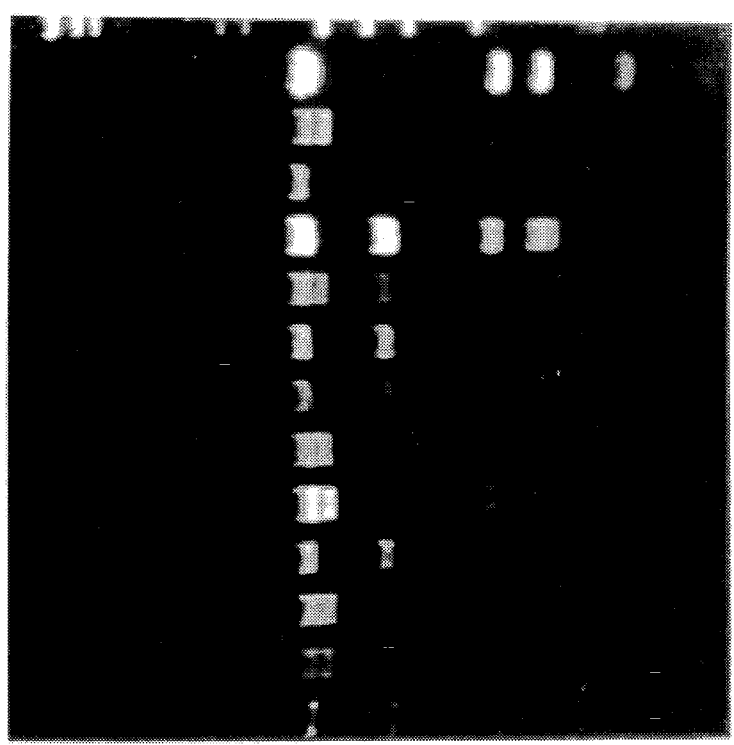
FIGS. 4A and 4B: Cloning of amplified DNA. Products of PCR mutagenesis containing the mutagenic primer 2039 at 1:250 and 1:50 ratios were cloned in pUC12N and DNA from individual clones were tested by HinF I digestion. Panel A: Clones derived from reaction products containing the mutagenic primer at a 1:250 ratio. Panel B: Clones derived from a reaction containing the mutagenic primer at a 1:50 ratio. The digestion of DNA from the clones containing the mutant inserts yields a 950 bp diagnostic band (shown by arrow). The mutant clones identified by this strategy are in lanes marked with an asterisk at the bottom. One lane marked with two asterisks contained HinF I digestion products diagnostic of both mutant and normal DNA (see above discussion). Lanes marked C, HinF I digested pUC12N DNA. Lane M: size markers (mixture of θX Hae III and λ Hind Ill).
Figure 4A:
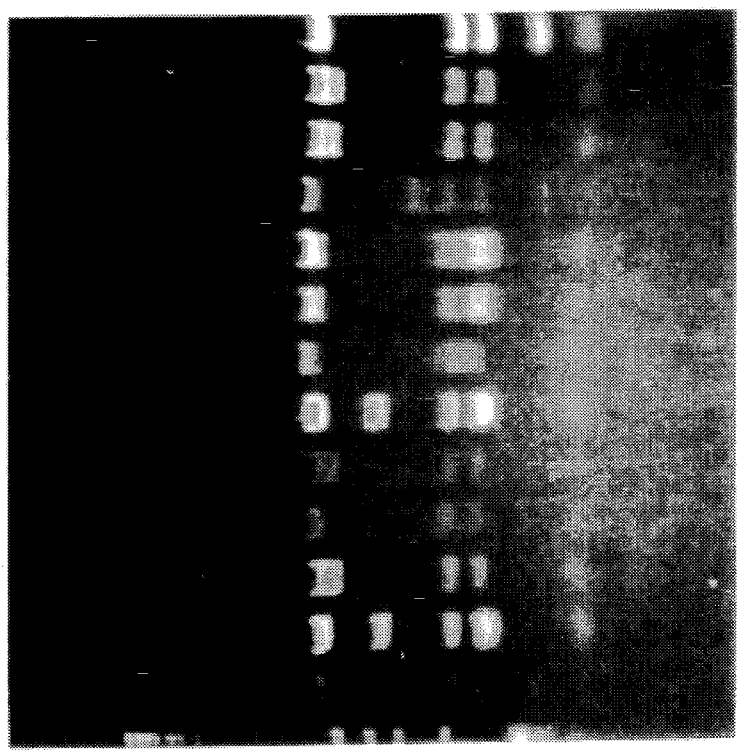

Representative analysis of the products of reactions containing primer 2039 at 1:250 or 1:50 ratios are shown in FIGS. 4A and 4B, respectively. The wild-type and mutant recombinants can be readily distinguished by HinF I digestion of the plasmid DNA. The wild type plasmid generates a diagnostic 1.3 Kb band and the plasmids containing trk sequences mutated by a Cys→Ser change at amino acid residue 345 exhibit a 975 bp band that is diagnostic of a T→A change that created a new HinF I site. In the clones derived from the amplification products of a reaction containing the mutant primer at 1:250 ratio, 2 of 5 recombinants carried the mutation (FIG. 4A). Six of the 11 recombinants derived by cloning PCR products with the mutagenic primer at a 1:50 ratio carried the desired mutation (FIG. 4B). One of these clones (Clone 9, FIG. 4B) appeared to be a mixture of mutant and wild-type sequences, evident by the appearance at the equimolar ratio of both the 1.3 and the 975 bp diagnostic bands. This clone was apparently generated by transformation of E. coli with a heteroduplex between wild-type and mutant strands of DNA.

EXAMPLE 6

Efficiency of Mutagenesis

Figure 5:
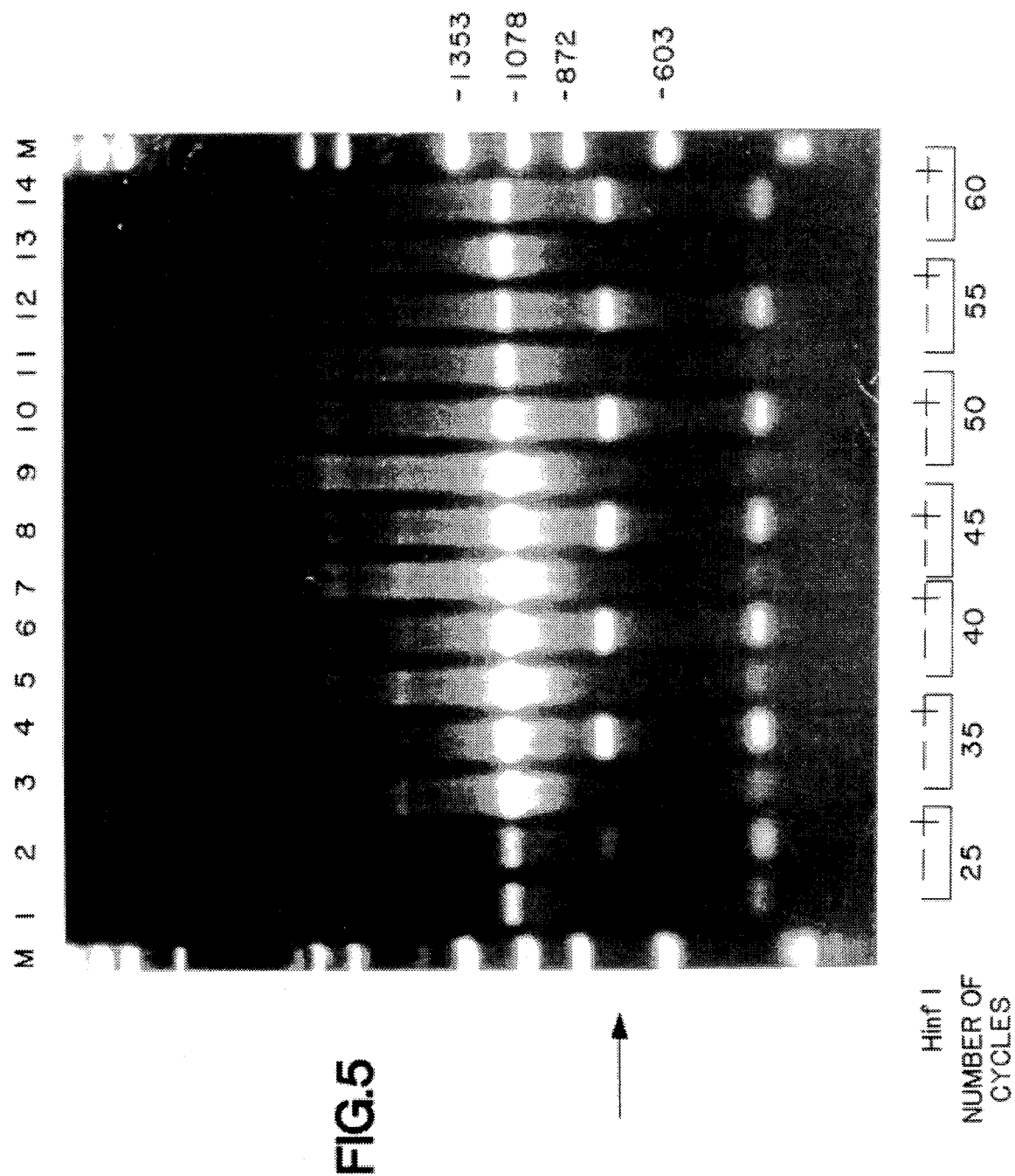
FIG. 5: Effect of the degree of amplification on the efficiency of mutagenesis. A 1.1 Kb segment of the trk protooncogene was amplified to mutate a Cys residue to Ser. Primers 1709, 1712 and 2039 were used at a 1:1:250 ratio in 7 different amplification reactions. Each reaction was amplified for the number of cycles indicated at the bottom. Aliquots of each reaction were tested by the HinF I RFLP assay. The undigested (−) and HinF I digested (+) DNAs from each reaction were compared by gel electrophoresis. The mutant DNA is cut with HinF I to produce an indicator band of 750 bp (shown with an arrow). Lanes M contain molecular-size markers and the size (bp) of some of these are shown on the right.

Since efficient amplification of cloned DNA templates cab be achieved in less than 40 cycles of PCR and because the error rate due to misincorporation has been reported to be higher during later rounds of amplification, we tested the effect of the level of amplification on the efficiency of mutagenesis. A set of reactions containing primers 1709, 1712 and 2039 (at a 1:250 ratio) were amplified for 25, 35, 40, 45, 50, 55 and 60 cycles. Aliquots of each reaction were tested by HinF I digestion. Results are shown in FIG. 5. Mutant products were detectable in all the reactions, including one in which only 25 cycles of PCR were carried out. As expected, the total yield of the amplified product is greater after more cycles of amplification. However, the ratio of wild-type and mutant molecules at different levels of amplification in this experiment appears to be more or less constant. We cloned amplified products obtained after 25, 40 and 60 cycles of PCR. In each case the efficiency of mutagenesis was better than 50%. These results indicate that the mutation can be efficiently incorporated after moderate levels of amplification.

EXAMPLE 7

Direct Mutagenesis of Sequences Cloned in Vectors

Figure 6B:
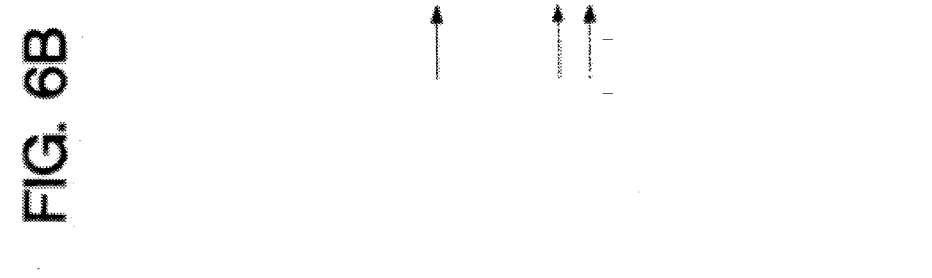
FIG. 6B: Direct mutagenesis of genomic DNA. A 1.4 Kb segment of the human $\beta_2$-adrenergic receptor was amplified by PCR from a genomic DNA template. Three primers were used (Table 1), including the mutagenic primer at different concentrations in separate reactions as indicated. The 1.4 Kb mutant and wild-type products (solid arrow) are distinguished by Bgl II digestion. The wild-type DNA is cut into two fragments of 800 and 600 bp (dashed arrows). The mutant DNA is resistant to BglII digestion. −=no Bgl II; +=Bgl II digestion; M=lanes containing molecular size markers (mixture of θx Hae III and λ Hind III). The molecular sizes of some of the markers are indicated on the right.
Figure 6A:
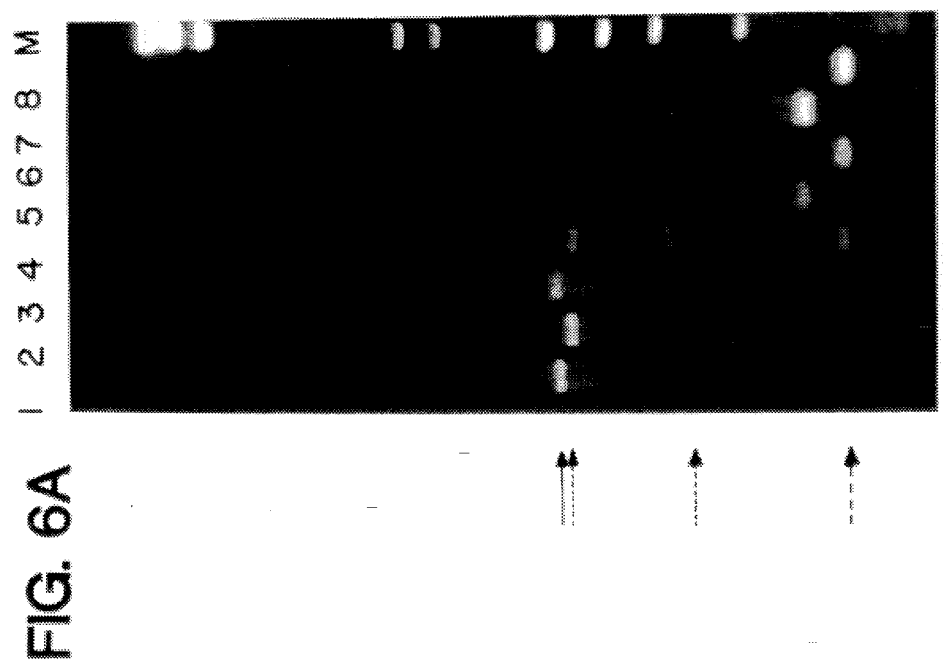
FIG. 6A: Mutagenesis employing pUC sequencing primers. The forward and reverse sequencing primers and various concentrations (indicated at the bottom) of the mutagenic 2039 primer were used to amplify a trk gene sequence cloned in pUC12N. The 1.2 Kb amplified DNA product (solid arrow) was digested with HinF I to distinguish between mutant and wild-type products. The HinF I digestion products are indicated with dashed arrows. The wild-type DNA sequences are cut once and mutant DNA is cut twice with HinF I. The 750 and 350 bp digestion products of the mutant DNA and the 1.1 Kb product of the wild-type DNA are visible in this gel and are indicated with dashed arrows.
Figure 7B:
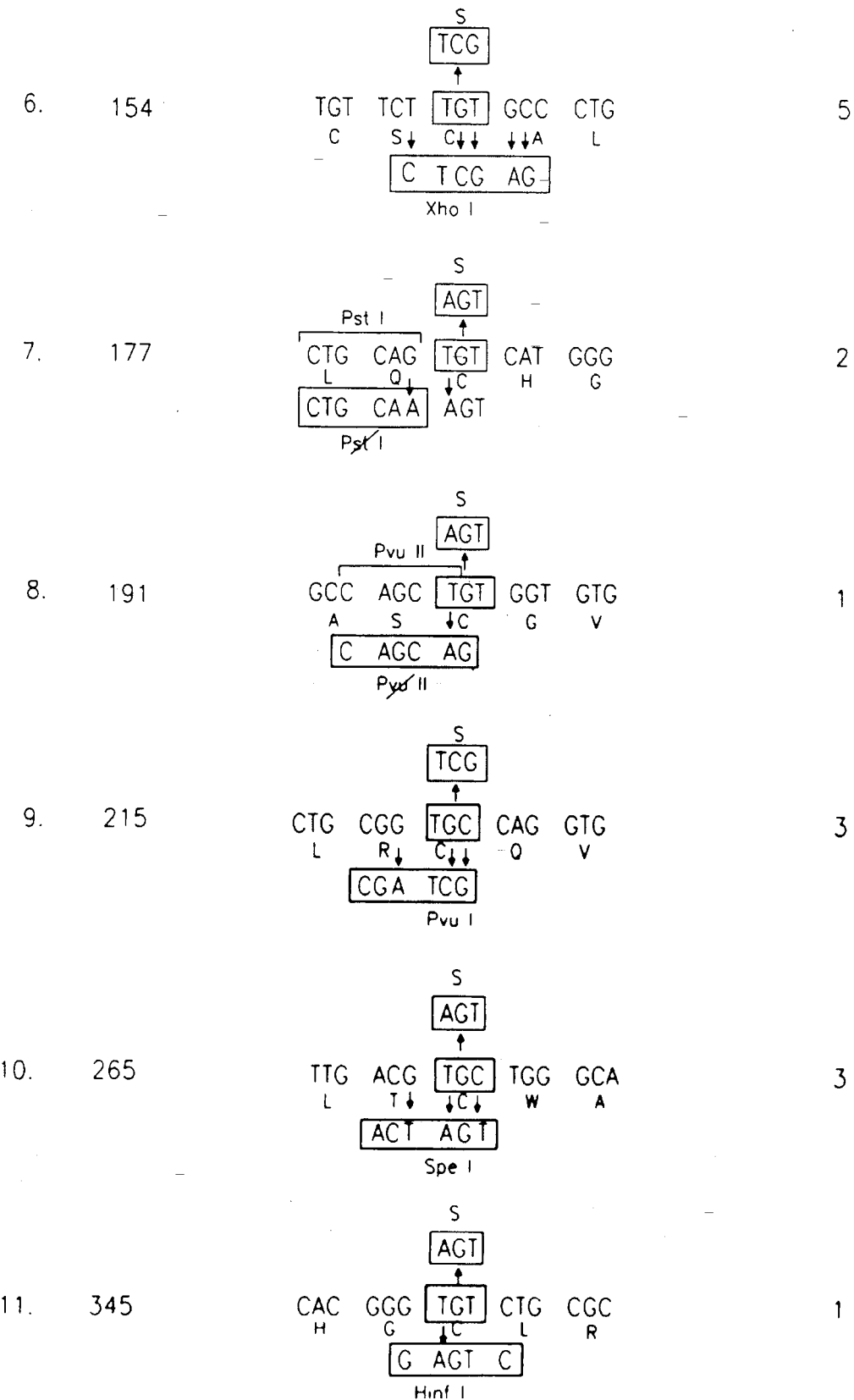
FIG. 7: Design of restriction fragment length polymorphisms at the site of mutagenesis. The 11 cysteine residues located in the extracellular domain of the human trk protooncogene were targeted for mutagenesis by the method described above. In each case, the sequence mismatches required to create the Cys→Ser change and to generate an RFLP diagnostic of the mutation are shown. The mismatches are shown by arrows and the created (or destroyed) restriction sites are boxed. The amino acids are shown in the single letter code. The number of mismatches required for the design of each primer is indicated. The primers corresponding to the sequence in lane 11 was used in the experiments shown in FIGS. 3–6. The primers in lanes 5 and 10 were also successfully tested.

Standard cloning vectors such as pUC and related plasmids (pBluescript, etc.) or bacteriophages (M13 or λ) are commonly used as a starting point for sequence and mutation analysis. The possibility of using standard sequencing primers in combination with specific mutagenic primers for the direct mutagenesis of sequences cloned in such vectors was tested. A 1.1 Kb segment of the human trk cDNA cloned in the vector pUC12N was used as a template for mutagenesis with primer 2039 (Table 1, see above). For PCR, the sequencing primers (forward and reverse) and various concentrations of the mutagenic primer were employed. Amplification for 40 cycles was followed by HinF I digestion and gel analysis. One tenth of the amplified DNA was digested with 10 units of HinF I under conditions suggested by the manufacturer (New England Biolabs). The digestion products were analysed on agarose gels. Results are shown in FIG. 6A.

The wild-type amplification product, approximately 1.1 Kb, contains a HinF I site located in the poly-linker of the cloning plasmid. The presence of this HinF I site in the poly-linker allows for easy monitoring of the efficiency of enzyme digestion. The mutant products, in addition, carry a second HinF I site at the site of mutagenesis. This permits easy identification of the mutant molecules in the amplified products. The presence of this HinF I site in the poly-linker allows for easy monitoring of the efficiency of enzyme digestion. Amplification using these three primers resulted in the efficient production of mutant and wild-type trk sequences in this experiment (FIG. 6A). These results indicate that universal sequencing primers can be used in conjunction with gene-specific mutagenic primers for the introduction of mutations into cloned sequences.

EXAMPLE 8

Direct Mutagenesis of Genomic DNA

The most significant provision of PCR mutagenesis protocols is the capability of direct mutagenesis of genomic DNA and cDNA sequences. The mutagenesis protocol was tested using genomic DNA as a template. The β-adrenergic receptor gene was used to illustrate this application. Emorine, L. J. et al., Proc. Natl. Acad. Sci. USA 89, 6995–6999 (1987). The complete coding sequence of the β-adrenergic receptor gene (which lacks an intron) can be amplified by using a pair of PCR primers from a cDNA prepared from the A431 cell-line or human genomic DNA (Table 1). A mutagenic primer was designed that was complimentary to the sequences in the cytoplasmic domain of the beta adrenergic receptor gene. This primer contained a single point mutation that was designed to abolish a unique Bgl II site in the gene without altering the encoded amino acids (Table 1). Incorporation of this mutagenic primer, therefore, can be monitored by RFLP analysis of the PCR products. Human genomic DNA (100 ng aliquots) was used in PCR reactions containing the two PCR primers and various ratios of the mutagenic third primer. After 40 cycles of PCR, aliquots from each reaction were tested by Bgl II digestion and electrophoresis. Results are shown in FIG. 6B.

The 1.4 Kb amplified sequence is cleaved once by Bgl II, generating approximately 800 and 600 bp fragments. The incorporation of the mutagenic third primer results in the generation of a subset of amplified products lacking this Bgl II site and therefore products which are resistant to Bgl II cleavage. This experiment illustrates two features of the disclosed system of mutagenesis: mutagenesis of genomic sequences is possible without prior cloning, and both the generation and the extinction of restriction enzyme sites can be used as a diagnostic test for the analysis of mutants.

EXAMPLE 9

Generation of Restriction Fragment Length Polymorphisms in Combination with Mutagenesis The use of restriction fragment length polymorphisms in combination with mutagenesis for the assessment of the efficiency of mutagenesis after PCR amplification was also examined.

To illustrate this principle, primers were designed directed to mutate each of the 11 cysteine residues in the extracellular domain of the human trk protooncogene. Each of these primers was expected to create a Cys→Serine change at a specific position and to simultaneously generate a diagnostic restriction polymorphism. Sequences of these primers in the region of interest are shown in Table 1. The created polymorphisms either generate a new restriction site or destroy a pre-existing site as a result of 1–5 specific mismatches in the sequence. In 4 of the 11 cases, the generated RFLP is a direct result of the mismatches required to produce a Cys→Ser change. In 6 other cases, mismatches were also introduced outside the Cys codon in order to generate the RFLP. In one case, the RFLP was not related to the Cys codon mutation, but was a consequence of a third base silent change in a neighboring codon. This clearly illustrates the potential of the method. Even in such a constrained situation (a requirement of a specific amino-acid change, e.g. Cys→Ser), it is possible to create a useful RFLP in each of the 11 cases examined by introducing fewer than 5 changes in the coding sequences.

What is claimed is:

1. A method for the incorporation of mutations into one or both strands of a target double stranded DNA molecule derived from a starting nucleic acid molecule comprising:

(a) contacting the target double stranded DNA molecule derived from a starting nucleic acid molecule simultaneously with two primers flanking the nucleotides to be mutated and a mutagenic third primer; and (b) subjecting the resulting reaction mixture to a sufficient number of rounds of PCR to generate the mutations in one or both strands of the target double stranded DNA molecule and amplify the mutated DNA sequence.

2. The method according to claim 1 wherein the starting nucleic acid molecule is genomic DNA.

3. The method according to claim 1 wherein the starting nucleic acid molecule is RNA.

4. The method according to claim 3 wherein the RNA is messenger RNA.

5. The method according to claim 1 wherein the starting nucleic acid molecule is complementary DNA.

6. The method according to claim 1 wherein the starting nucleic acid molecule is a DNA-RNA hybrid.

7. The method according to claim 1 wherein the nucleic acid sequence to be mutated is a portion of the double stranded DNA molecule derived from the starting nucleic acid molecule.

8. The method according to claim 1 wherein the nucleic acid sequence to be mutated constitutes the entire double stranded DNA molecule derived from the starting nucleic acid molecule.

9. The method according to claim 1 wherein the starting DNA is unpurified.

10. The method according to claim 1 wherein the starting nucleic acid molecule is plasmid DNA.

11. The method according to claim 1 wherein the starting nucleic acid molecule is cloned DNA.

12. The method according to claim 1 wherein the mutagenic primer contains a single mismatch.

13. The method according to claim 1 wherein the mutagenic primer contains more than one mismatch and wherein the mutagenic primer is able to hybridize to the target double stranded DNA molecule.

14. The method according to claim 1 wherein one or both of the flanking primer contain one or more mismatches and wherein the flanking primers are able to hybridize to the target double stranded DNA molecule.

15. The method according to claim 1 wherein the number of rounds of PCR ranges from 3 to about 60.

16. The method according to claims 1, 12 or 13 wherein the mutagenic third primer is used to generate a diagnostic restriction enzyme site or eliminate an existing diagnostic restriction enzyme site.

17. A method for the incorporation of mutations into one or both strands of a target double stranded DNA molecule derived from a starting nucleic acid molecule comprising:

(a) separating the strands of the target double stranded DNA molecule by physical, chemical or enzymatic means;

(b) contacting the resulting single stranded DNA molecules simultaneously with two oligodeoxyribonucleotide primers flanking the nucleotides to be mutated and a mutagenic third oligodeoxyribonucleotide primer under conditions such that an extension product of each primer is synthesized using an inducing agent;

(c) separating the primer extension products by physical, chemical or enzymatic means from the templates on which they are synthesized; and (d) treating the single stranded molecules generated from step (c) with the three primers of step (b) under conditions such that a primer extension product is synthesized using on inducing agent.

18. The method according to claim 17 wherein the inducing agent is Taq DNA polymerase.

19. The method according to claim 17 wherein steps (c) and (d) are repeated at least once.

* * * * *